United States Patent
Steckel et al.

(10) Patent No.: US 7,533,630 B2
(45) Date of Patent: May 19, 2009

(54) ANIMAL LITTER HAVING THE PROPERTY OF DETECTING DIABETES IN FELINES

(75) Inventors: Ralph J Steckel, Dallas, TX (US); Larry J Murphy, Richardson, TX (US)

(73) Assignee: Pet Ecology Brands, Inc., Dallas, TX (US)

( * ) Notice: Subject to any disclaimer, the term of this patent is extended or adjusted under 35 U.S.C. 154(b) by 0 days.

(21) Appl. No.: 11/843,515

(22) Filed: Aug. 22, 2007

(65) Prior Publication Data

US 2008/0087226 A1    Apr. 17, 2008

Related U.S. Application Data

(60) Provisional application No. 60/823,228, filed on Aug. 22, 2006.

(51) Int. Cl.
*A01K 1/01* (2006.01)
(52) U.S. Cl. ..................................... 119/165
(58) Field of Classification Search ................ 119/165, 119/171, 172, 173; 436/95
See application file for complete search history.

(56) References Cited

U.S. PATENT DOCUMENTS

| 4,326,481 | A | * | 4/1982 | Gruss | ......................... 119/171 |
|---|---|---|---|---|---|
| 5,143,023 | A | * | 9/1992 | Kuhns | ......................... 119/173 |
| 5,267,532 | A | * | 12/1993 | Franklin et al. | ............. 119/173 |
| 5,359,960 | A | * | 11/1994 | Yananton | ..................... 119/165 |
| 5,371,054 | A | * | 12/1994 | Pluta et al. | ..................... 502/62 |
| 5,655,480 | A | * | 8/1997 | Steckel | ........................ 119/171 |
| 5,685,259 | A | * | 11/1997 | Santioemmo et al. | ....... 119/172 |
| 5,780,385 | A | * | 7/1998 | Santioemmo et al. | ....... 119/172 |
| 5,830,765 | A | * | 11/1998 | Santioemmo et al. | ......... 436/66 |
| 5,900,379 | A | * | 5/1999 | Noda et al. | .................. 436/518 |
| 6,063,637 | A | * | 5/2000 | Arnold et al. | ................. 436/94 |
| 6,308,658 | B1 | * | 10/2001 | Steckel | ........................ 119/173 |
| 7,307,053 | B2 | * | 12/2007 | Tasz et al. | .................... 510/384 |

* cited by examiner

*Primary Examiner*—Yvonne R. Abbott
(74) *Attorney, Agent, or Firm*—Howison & Arnott, L.L.P.

(57) ABSTRACT

An animal litter composition comprised of a liquid absorbent aggregate impregnated with an agent to indicate the presence of sugar in the urine of felines and other related species includes 88.1 percent +/−5.0 percent by weight of an expanded aggregate, 00.9 percent +/−0.7 percent by weight of an odor control/antistatic agent, 07.0 percent +/−4.0 percent by weight of a clumping agent, 03.0 percent +/−2.5 percent by weight of a surfactant; and 01.0 percent +/−0.90 percent by weight of a glucosuria indicator. A method of detecting glucosuria in a feline includes providing the animal litter in a litter box or in an enclosure in which the feline is restrained until the feline urinates on the litter and then visually observing the litter for a color change.

17 Claims, No Drawings

ANIMAL LITTER HAVING THE PROPERTY OF DETECTING DIABETES IN FELINES

CROSS-REFERENCE TO RELATED APPLICATION

This application claims the benefit of U.S. Provisional Application for Patent Ser. No. 60/823,228, filed Aug. 22, 2006, and entitled ANIMAL LITTER HAVING THE PROPERTY OF DETECTING DIABETES IN FELINES the disclosure of which is incorporated herein by reference.

TECHNICAL FIELD

This disclosure relates to an animal litter in which a liquid absorbent aggregate acts as a carrier for an agent for detecting certain illnesses or conditions in animals, and in particular, diabetes.

BACKGROUND

An ever-increasing number of households keep a variety of domestic animals as house pets. One favorite house pet is the domestic cat. Domestic cats and related species (collectively known as "felines") are, however, susceptible to a number of diseases, including diabetes mellitus ("sugar diabetes"), a common endocrine disorder. Over the years, improved nutrition and care have resulted in the extension of life expectancies for household pets, including felines. With increased age, felines, particularly overweight and female animals, become more susceptible to diabetes.

Diabetes is typically caused either by insufficient production of the hormone insulin by the pancreas (type 1 diabetes) or by inadequate response of the body's cells to insulin (type 2 diabetes). Since a diabetic cat is not able to utilize glucose properly, the cat will ultimately develop hyperglycemia e.g., high blood sugar levels and subsequent glucosuria (sugar in the urine). The glucosuria leads to polyuria (excessive urination) and polydipsia (excessive thirst). In spite of maintaining a good appetite, diabetic cats lose weight because the body's tissues are unable to utilize glucose properly.

Feline diabetes may result in a dangerous, sometimes fatal condition called ketoacidosis, indicated by loss of appetite, vomiting, diarrhea, lethargy, weakness, dehydration, and breathing abnormalities. Additionally, diabetes can lead to an unhealthy skin and coat, liver disease, and secondary bacterial infections. A diabetes-related disorder called diabetic neuropathy may cause cats to become progressively weaker, especially in the hind legs, impairing their ability to jump and causing them to walk with their hocks touching the ground. Progression of the disease ultimately leads to further metabolic disturbances including vomiting, loss of appetite, weakness, dehydration and death.

In the field of veterinarian medicine and treatment it is very important to have tests or indicators to promptly identify and treat ailments and diseases. It goes without saying that the animal cannot communicate most ailments, so it is important to be able to easily detect a malady such as diabetes as soon as possible. Due to the growing number of domestic cats that are kept as house pets, there is an increasing need for a simple means to enable the cat owner to detect the possibility of feline diabetes so that curative steps can be taken to avoid serious illness in the animal.

U.S. Pat. No. 6,382,132 to Steckel, issued May 7, 2002, the disclosure of which is incorporated herein for all purposes, describes an animal litter including a liquid absorbent aggregate impregnated with a litmus agent for indicating a urinary track infection in felines. The litmus material possesses an activity range from pH 6.6 to pH 8.0 as provided by, but not limited to, sodium phenolsulfonephthalein.

SUMMARY

In one embodiment, an animal litter composition according to the disclosure includes a liquid absorbent aggregate impregnated with an agent to indicate the presence of sugar in the urine of felines and other related species. In one variation, the litter composition includes:
  88.1 percent +/−5.0 percent by weight of an expanded aggregate;
  00.9 percent +/−0.7 percent by weight of an odor control/antistatic agent;
  07.0 percent +/−4.0 percent by weight of a clumping agent;
  03.0 percent +/−2.5 percent by weight of a surfactant; and
  01.0 percent +/−0.90 percent by weight of a glucosuria indicator.

In one variation, the glucosuria indicator is anthrone. In another variation, the glucosuria indicator is glucose oxidase and one or more hydroxide reactive reagents. The aggregate may be a clay, or an expanded aggregate selected from the group consisting of perlite, vermiculite, herculite, rice hulls and zeolite. The odor control/antistatic agent may be an n-alkyl dimethyl benzyl ammonium chloride, dialkyl dimethyl ammonium chloride or a combination thereof. In another aspect, the surfactant may be an ethoxalated fatty alcohol, an alkylphenol ethoxylate or a combination thereof.

In one selected embodiment, the component parts of the litter composition are present in the following weight percentages:
  88.6 percent by weight of expanded aggregate;
  00.9 percent by weight of odor control/antistatic agent;
  07.0 percent by weight of clumping agent;
  03.0 percent by weight of surfactant; and
  00.5 percent by weight of a glucosuria indicator.

In another variation, a method of identifying the presence of sugar in the urine of felines and other related species includes the steps of providing a litter composition to be used by the feline for the purpose of urination thereon. The litter composition includes a major portion of an expanded aggregate and minor portions of an odor control/antistatic agent, a clumping agent, a surfactant and a glucosuria indicator. After the feline has urinated on the litter composition, the composition is visually observed for a color change that may indicate the presence of sugar in the feline's urine. In one variation the litter composition has a normal color that varies from a pale yellowish gray to white and the litter composition contacted with urine containing sugar changes to a color distinguishable from the color of the remaining litter composition, i.e., non-contacted or contacted by urine not containing sugar.

DETAILED DESCRIPTION

According to the disclosure, there is provided an animal litter comprised of a liquid absorbent aggregate that has been treated with an agent to visually indicate the presence of an endocrine disorder, specifically diabetes, in cats and other felines. The presence of diabetes in the cat is represented by glucosuria (sugar in the urine). Impregnating the cat's litter with a glucosuria indicator that changes color in response to sugar in the cat's urine, enables the pet owner to determine if there is a possibility that his or her pet has diabetes. Once the owner has observed the change of coloration of clumped litter containing the urine, the owner may decide whether or not the pet should be tested for diabetes. If so, the pet can be taken immediately to a veterinarian for the appropriate tests and if necessary, treatment.

The glucosuria indicator system disclosed herein is believed to be effective with all known animal litters among them being various clays such as those based chiefly upon clay minerals, kaolin, illite, attapulgite, and the like. The indicator available in powdered form may be used by incorporation into the powders of the litter. It may also be made into a solution which is sprayed on to the surface of an aggregate. The indicator may also be used with light weight aggregates such as perlite, vermiculite, herculite rice hulls, and zeolite. In one variation, the indicator may be used in connection with litter compositions described and claimed in U.S. Pat. No. 6,382,132, the disclosure of which is incorporated herein by reference, and similar litter compositions.

Animal litters according to the present disclosure include compositions comprised of a liquid absorbent aggregate impregnated with an agent for detecting glucosuria in cats. The indicator material reacts to sugar in the cat's urine to change the color of the litter where the cat has voided to indicate to the pet owner the presence of or potential presence of diabetes. In one variation the glucosuria indicator is anthrone (9, 10-dihydro-9-oxoanthracene).

In another variation, the glucosuria indicator may be glucose oxidase used with one or more hydroxide reactive reagents that change color when oxidized. In one variation the hydroxide reactive reagents include a peroxidase and a potassium iodide chromogen. When a litter composition using a glucose oxidase indicator is contacted with sugar containing urine, the glucose oxidase catalyzes the formation of gluconic acid and hydrogen peroxide from the oxidation of glucose. A second enzyme, the peroxidase, catalyzes the reaction of hydrogen peroxide with potassium iodide chromogen to oxidize the chromogen to colors ranging from blue through greenish-brown, and brown to dark-brown. The color change of the portion of the litter composition contacted with sugar containing urine is visibly detectable.

In one variation, an animal litter incorporating features of the present disclosure comprises an expanded light weight aggregate, a clumping agent, a surfactant, an odor control agent and the glucosuria indicator. The composition is dust free and light weight. The animal litter includes a clumping agent so that after use, a bioclumped mass including the animal's urine may be scooped from the dry litter and flushed down the commode. The composition includes glucosuria indicator coated granules that react to sugar in the cat's urine and change color to indicate the possible presence of a diabetic condition. If the indicator is anthrone, the color of the litter may change to a bluish shade. If such a color change is detected, the pet owner should immediately take the cat for examination and treatment by a veterinarian.

According to one aspect, a light weight aggregate used in the formulation of the litter is selected from the class consisting of perlite, vermiculite, herculite rice hulls, and zeolite. In one variation, perlite is the selected aggregate. Perlite may be obtained from Harborlite Corporation, 1950 East "W" Ave, Vicksberg, Mich. Perlite is expanded to provide a light weight aggregate having porous surfaces by heating to approximately 1800° F. In one embodiment, the aggregate comprises from about 83 percent to about 93 weight percent of the litter composition.

Due to variations in raw materials, the color of the aggregate used in the formulation of the litter compositions described herein will vary. Consequently, glucosuria indicators used with the litter compositions should react with sugar in the urine of an animal using the litter in a manner to generate a change in color that is distinguishable from the color of the aggregate (whether wet or dry). In the case of perlite, the normal color may vary from white to a pale yellow grey. Hence, glucosuria indicators used in the compositions including perlite should generate a color on contact with sugar containing urine different from the normal white to pale yellow grey and with sufficient intensity to be visually detectable.

In order to enable the litter composition to agglomerate into a mass upon contact with animal urine, a clumping agent is mixed with the litter composition, preferably in an amount ranging from about 1 percent to about 10 percent by weight of the litter composition. In one embodiment, the clumping agent is a polymeric viscosity modifier, such as a guar gum or derivatized guar, for example AgRho DR-2000 available from Rhone-Poulenc, prospect Plains Road, Cranbury, N.J. 0851-7600.

In one embodiment, the surfactant is a C-10 to C-18 ethoxalated fatty alcohol available from Tomah Products, Inc., 337 Vincent Street, Milton, Wis. 53563. Other surfactants such as alkylphenol ethoxylates may be employed. The surfactant adds the property of anti-tracking to the composition thus preventing the carrying of portions of the composition from the litter box to other areas of the household. In one embodiment, the surfactant comprises from about 0.5 to about 5.5 weight percent of the litter composition.

Also included in the litter composition is an odor control/antistatic agent. In one embodiment, the odor control/antistatic agent may be an n-alkyl dimethyl benzyl ammonium chloride or dialkyl dimethyl ammonium chloride available from Stepan Corporation, Northfield, Ill. 60093. The odor control agent performs the function of odor elimination by blocking odor producing oxidation of decomposing organic matter and/or by complexing airborne odor molecules. The odor control/antistatic agent performs the function of odor elimination, not as a cover-up, but in the prevention of the formation of the ammonical odors. In other variations, non-ionic esters or amines such as glycerol esters of fatty acids may be employed as odor control agents. In one embodiment, the odor control/antistatic agent comprises from about 0.2 weight percent to about 1.6 weight percent of the litter composition.

In one variation, formulations of animal litters according to the present disclosure may be as follows:
 88.1 percent +/−5.0 percent by weight of expanded aggregate;
 00.9 percent +/−0.7 percent by weight of odor control/antistatic agent;
 07.0 percent +/−4.0 percent by weight of clumping agent;
 03.0 percent +/−2.5 percent by weight of surfactant; and
 01.0 percent +/−0.90 percent by weight of a glucosuria indicator.

In another variation, a selected composition includes:
 88.6 percent by weight of expanded aggregate;
 00.9 percent by weight of odor control/antistatic agent;
 07.0 percent by weight of clumping agent;
 03.0 percent by weight of surfactant; and
 00.5 percent by weight of a glucosuria indicator.

In one embodiment, a glucosuria indicator solution is prepared by dissolving the glucosuria indicator in the surfactant and a suitable non-ionic solvent such as mineral oil. After the indicator is dissolved, the indicator is applied to the aggregate in a manner to insure adequate dispersion and coverage of the aggregate granules. In one variation, the glucosuria indicator solution is sprayed onto the aggregate.

The animal litter composition is prepared by mixing the above-listed components in sufficient quantity to make 100 weight percent in a mixing apparatus which causes the odor control/antistatic agent, the glucosuria indicator solution and the clumping agent to enter and to fill the pores in the expanded aggregate. The mixing apparatus may be used to provide multiple folds per revolution during the mixing process. A suitable mixing apparatus is a Continental Roto Mixer, Model V5, drum type mixer. The mixing apparatus rotates at 4 RPM. Each revolution provides six folds in the mixing action to assure that the particles of expanded aggregate are adequately coated with the odor control/antistatic agent, the glucosuria indicator solution and the clumping agent.

When a feline having glucosuria urinates on animal litter compositions as disclosed herein the litter contacted by the urine will change color so as to be distinguishable from the remainder of the litter, indicating the presence of sugar in the urine. In one embodiment, the normal color of the litter compositions will vary from a pale yellow-grey to white. In the compositions including anthrone as a glucosuria indicator, when contacted with sugar-containing urine, the color of the contacted litter may change to a bluish color, or assume a bluish hue, having sufficient intensity to enable visual detection of the color change. The exact color change and the intensity of the color change may vary depending including the exact composition of the litter, the amount of sugar in the urine, variations in raw materials and other factors, however, the change will be sufficient to enable a user to visually distinguish litter contacted with sugar containing urine from the remainder of the litter, i.e., non-contact portions and/or portions contacted by urine not containing sugar.

The composition is packaged or shipped in sealed bags which have been placed in cardboard shipping containers or pails so that the vibration encountered during shipping does not cause the components to separate. The sealed bags also prevent any of the components from drying out during transit or storage.

A method of identifying the presence of sugar in the urine of felines and other related species includes the steps of providing a litter composition to be used by the feline for the purpose of urination thereon. Where the feline is a house pet, the litter composition is typically made available to the feline in a litter box placed in an unobtrusive area. In other cases the litter may be provided in a container or on the floor of a cage or similar enclosure in which the feline is restrained for the purpose of determining whether the animal has glucosuria or for other reasons.

The litter composition utilized in the method generally includes a major portion of an expanded aggregate and minor portions of an control/antistatic agent, a clumping agent, a surfactant and a glucosuria indicator. As used herein, a major portion is greater than 80 weight percent and a minor portion is less than 10 weight percent. In other variations, the method utilizes compositions having the formulations set forth above. After the feline urinates on the litter composition, whether in a litter box or in an enclosure, the composition is visually observed for a color change. A change in the color of the urine-contacted litter that is visually distinguishable from the color of the non-contacted litter or litter contacted by non-sugar containing urine may indicate the presence of sugar in the feline's urine. Upon observing a distinguishable color change, the owner may wish to take the feline to a veterinarian for further tests and/or treatment.

In one variation the normal color of the perlite or other appropriate aggregate used disclosed herein varies from a pale yellowish gray to white. Therefore the glucosuria indicator should change to a color distinguishable from the normal color (whether wet or dry) of the aggregate when contacted with urine containing sugar. In one variation, wherein the glucosuria indicator is anthrone, the litter composition may change to a bluish color or assume a bluish hue that is visually detectable and distinguishable from the normal color of the litter composition. In another variation, wherein the indicator is glucose oxidase used with one or more hydroxide reactive reagents, the color change may range from blue through greenish-brown, and brown to dark-brown. The exact color change may vary depending upon a number of factors; however, the portion of the litter composition contacted with sugar containing urine is visibly detectable and distinguishable from the non-contacted litter.

The drawings and detailed description herein are to be regarded in an illustrative rather than a restrictive manner, and are not intended to limit the following claims to the particular forms and examples disclosed. On the contrary, further modifications, changes, rearrangements, substitutions, alternatives, design choices, and embodiments will be apparent to those of ordinary skill in the art. Thus, it is intended that the following claims be interpreted to embrace all such further modifications, changes, rearrangements, substitutions, alternatives, design choices, and embodiments

We claim:

1. An animal litter composition comprised of a liquid absorbent aggregate impregnated with an agent to indicate the presence of sugar in the urine of felines and other related species wherein the components of the animal litter composition are present in the following percentages:
   88.1 percent +/−5.0 percent by weight of an expanded aggregate;
   00.9 percent +/−0.7 percent by weight of an odor control/antistatic agent;
   07.0 percent +/−4.0 percent by weight of a clumping agent;
   03.0 percent +/−2.5 percent by weight of a surfactant;
   01.0 percent +/−0.90 percent by weight of a glucosuria indicator comprising one of anthrone or glucose oxidase with one or more hydrogen peroxide reactive reagents; and
   wherein the expanded aggregate is impregnated with the glucosuria indicator.

2. The animal litter of claim 1 wherein upon contact with sugar containing urine, a contacted portion of the animal litter composition changes color sufficiently to be visually distinguishable from a non-contacted portion of the animal litter composition.

3. The animal litter of claim 1 in which the aggregate is an expanded aggregate selected from the group consisting of perlite, vermiculite, herculite, rice hulls and zeolite.

4. The animal litter composition of claim 1 wherein the odor control/antistatic agent comprises an n-alkyl dimethyl benzyl ammonium chloride, dialkyl dimethyl ammonium chloride or a combination thereof.

5. The animal litter composition of claim 1 wherein the surfactant comprises an ethoxalated fatty alcohol, an alkylphenol ethoxylate or a combination thereof.

6. An animal litter comprised of a liquid absorbent aggregate impregnated with an agent to indicate the presence of sugar in the urine of felines and other related species, wherein the component parts of the litter are present in the following weight percentages:
   88.6 percent by weight of an expanded aggregate;
   00.9 percent by weight of an odor control/antistatic agent;
   07.0 percent by weight of a clumping agent;
   03.0 percent by weight of a surfactant;
   00.5 percent by weight of a glucosuria indicator comprising one of anthrone or glucose oxidase with one or more hydrogen peroxide reactive reagents; and wherein the expanded aggregate is coated with the glucosuria indicator.

7. The animal litter of claim 6 in which the aggregate is an expanded aggregate selected from the group consisting of perlite, vermiculite, herculite, rice hulls and zeolite.

8. The animal litter composition of claim 6 wherein the odor control/antistatic agent comprises an n-alkyl dimethyl benzyl ammonium chloride, dialkyl dimethyl ammonium chloride or a combination thereof.

9. The animal litter composition of claim 6 wherein the surfactant comprises an ethoxalated fatty alcohol, an alkylphenol ethoxylate or a combination thereof.

10. A method of identifying the presence of sugar in the urine of felines and other related species comprising:
   providing a litter composition to be used by the feline for the purpose of urination thereon, the litter composition including a major portion of an expanded aggregate and minor portions of an odor control/antistatic agent, a clumping agent, a surfactant and a glucosuria indicator comprising one of anthrone or glucose oxidase with one or more hydrogen peroxide reactive reagents; and
   wherein the expanded aggregate is impregnated with the glucosuria indicator
      whereby upon contact with sugar containing urine, a contacted portion of the animal litter composition changes color sufficiently to be visually distinguishable from a non-contacted portion of the animal litter composition; and
   visually observing the litter composition for a color change after the feline has urinated on the composition.

11. The method of claim 10 wherein the litter composition has a normal color that varies from a pale yellowish gray to white and wherein litter composition contacted with urine containing sugar changes to a color distinguishable from the color of non-contacted litter composition.

12. The method of claim 10 wherein the litter composition contacted with urine containing sugar changes from the normal color to blue.

13. The method of claim 10 wherein the components of the animal litter composition are present in the following percentages:
   88.1 percent +/−5.0 percent by weight of an expanded aggregate;
   00.9 percent +/−0.7 percent by weight of an odor control/antistatic agent;
   07.0 percent +/−4.0 percent by weight of a clumping agent;
   03.0 percent +/−2.5 percent by weight of a surfactant; and
   01.0 percent +/−0.90 percent by weight of a glucosuria indicator.

14. The method of claim 10 wherein the component parts of the litter are present in the following weight percentages:
   88.6 percent by weight of an expanded aggregate;
   00.9 percent by weight of an odor control/antistatic agent;
   07.0 percent by weight of a clumping agent;
   03.0 percent by weight of a surfactant; and
   00.5 percent by weight of a glucosuria indicator.

15. The method of claim 10 wherein the glucosuria indicating agent is anthrone.

16. The animal litter of claim 10 wherein the glucosuria indicating agent is glucose oxidase and one or more hydrogen peroxide reactive reagents.

17. The method of claim 10 wherein the surfactant comprises an ethoxalated fatty alcohol, an alkylphenol ethoxylate or a combination thereof.

* * * * *